(12) United States Patent
Taché et al.

(10) Patent No.: US 7,785,108 B2
(45) Date of Patent: Aug. 31, 2010

(54) DENTURE ATTACHMENT SYSTEM

(75) Inventors: Richard Taché, Saint-Sauveur (CA); Gilbert Piccard, Laval (CA); Charles-André Taché, Mont St-Hilaire (CA); André Archambault, Mansonville (CA)

(73) Assignee: Innovation Tap Inc., Saint-Laurent (CA)

( * ) Notice: Subject to any disclaimer, the term of this patent is extended or adjusted under 35 U.S.C. 154(b) by 213 days.

(21) Appl. No.: 11/630,167

(22) PCT Filed: Jun. 21, 2005

(86) PCT No.: PCT/CA2005/000964

§ 371 (c)(1),
(2), (4) Date: Dec. 20, 2006

(87) PCT Pub. No.: WO2005/122946

PCT Pub. Date: Dec. 29, 2005

(65) Prior Publication Data

US 2008/0038694 A1      Feb. 14, 2008

Related U.S. Application Data

(60) Provisional application No. 60/580,699, filed on Jun. 21, 2004.

(51) Int. Cl.
*A61C 8/00* (2006.01)

(52) U.S. Cl. ...................................................... 433/173

(58) Field of Classification Search ................ 433/172, 433/173, 174, 181, 182, 177
See application file for complete search history.

(56) References Cited

U.S. PATENT DOCUMENTS

| 4,085,506 A | 4/1978 | Lew |
| 5,169,309 A | 12/1992 | Staubli et al. |

(Continued)

FOREIGN PATENT DOCUMENTS

| CA | 2007586 | 8/1995 |

(Continued)

*Primary Examiner*—Chris L Rodriguez
*Assistant Examiner*—Eric Rosen
(74) *Attorney, Agent, or Firm*—Ogilvy Renault LLP

(57) ABSTRACT

A denture attachment system includes an implant member adapted to be secured in a mandible such that a head of the implant member projects out of the mandible. A locking mechanism is adapted to be received in a denture so as to cooperate with the implant member to releasably secure the denture to the implant member. The locking mechanism has a receptacle for receiving the head of the implant member. A locking member is movable between a locking position in which the locking member blocks an access out of the receptacle by opposing a surface complementary to the shape of the head of the implant member to hold the implant member captive in the receptacle with points of contact between the head of the implant member and the locking member being diametrically opposed with respect to the head, and a release position in which the head of the implant member may enter/exit the receptacle).

14 Claims, 3 Drawing Sheets

U.S. PATENT DOCUMENTS

| | | |
|---|---|---|
| 5,234,341 A | 8/1993 | Johansen |
| 5,413,480 A | 5/1995 | Musikant et al. |
| 5,427,906 A | 6/1995 | Hansen |
| 5,503,557 A | 4/1996 | Sillard |
| 5,571,015 A | 11/1996 | Siegmund |
| 5,630,717 A | 5/1997 | Zuest et al. |
| 5,716,214 A | 2/1998 | Lund et al. |
| 5,749,732 A | 5/1998 | Sendax |
| 5,842,864 A | 12/1998 | Unger |
| 5,997,299 A | 12/1999 | Unger |
| 6,007,337 A | 12/1999 | Bauer |
| 6,685,473 B2 | 2/2004 | Weissman |
| 2004/0005530 A1 | 1/2004 | Mullaly et al. |

FOREIGN PATENT DOCUMENTS

| | | |
|---|---|---|
| EP | 0 580 945 | 1/1998 |
| EP | 0 893 105 | 1/2004 |

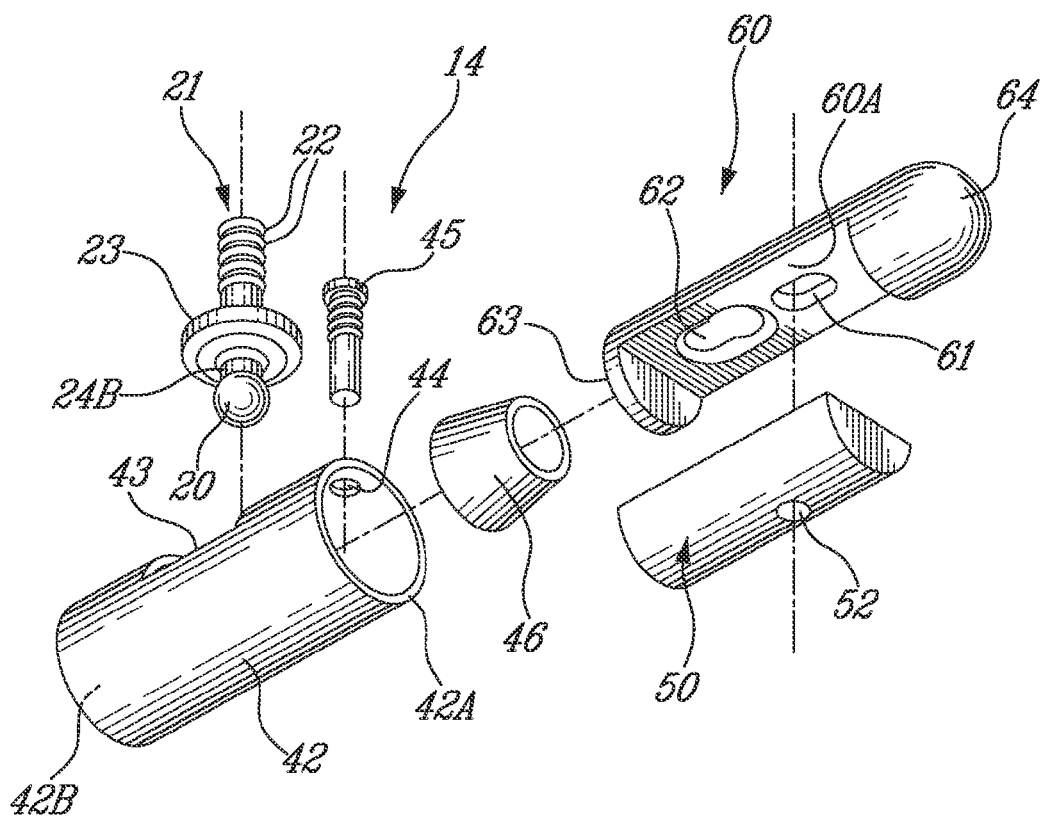
FIG. 3
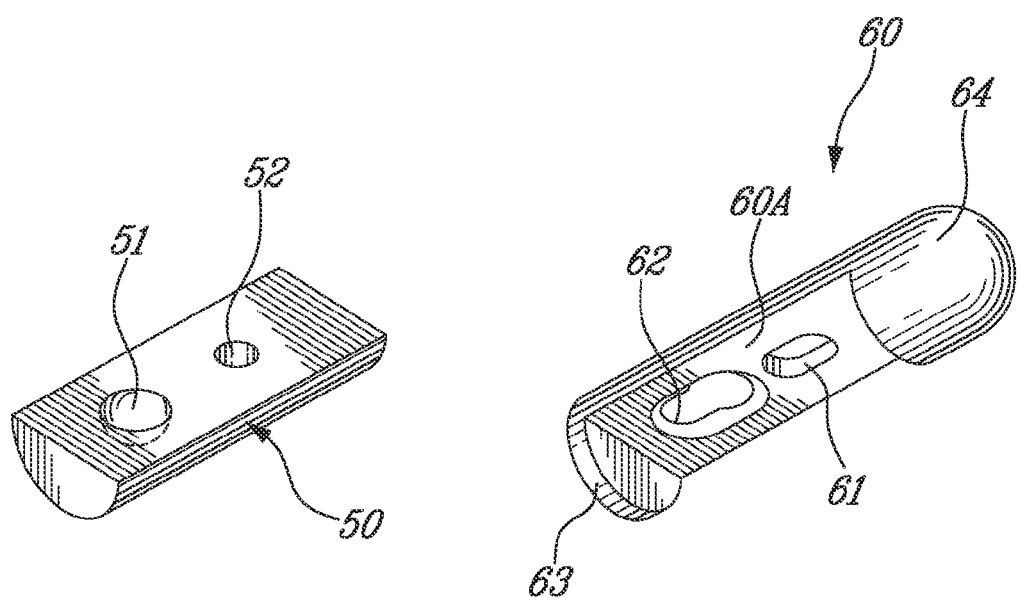
FIG. 4
FIG. 5

DENTURE ATTACHMENT SYSTEM

CROSS-REFERENCE TO RELATED APPLICATION

The present patent application is a 371 national phase application PCT/CA05/00964 filed 21 Jun., 2005 and claims priority on U.S. Provisional Patent Application No. 60/580,699, filed on Jun. 21, 2004, by the present applicants.

FIELD OF THE INVENTION

The present invention relates to dental prostheses, and more particularly, to a denture detachably mounted to permanent endosseous implants.

BACKGROUND OF THE INVENTION

It is known to provide permanently fixed dentures which include implants anchored in the mandible or maxilla osseous portions and a denture including an artificial gum and teeth structure being fixed to the implants and/or existing teeth or roots.

It is also known to provide a bridge or denture which includes a locking device adapted to lock onto the crown of a tooth. However, the torque which can be produced by the denture on the tooth or teeth by the function of the prosthesis can damage the crown of the tooth and render it useless.

It is also known to have a denture which is removably detached from an implant structure, wherein the implant structure includes a metallic arch or bar formed to bridge individual roots or root substitutes, such as pins implanted directly into the osseous material of the mandible or maxilla. The denture includes an artificial gum structure adapted to fit snugly over the arch and locking device for locking the denture to the arch. An example of such a device is described in U.S. Pat. No. 4,085,506, issued Apr. 25, 1978 to Isaih Lew. Such an assembly requires the arch to accommodate the locking device.

U.S. Pat. No. 5,716,214, granted on Feb. 10, 1998 to Lund et al., describes a dental prosthesis system in which a denture is removably secured to a mandible having permanent osseous implants. The interconnection between the denture and the implant is achieved by male/female members, that are releasable from one another when it is desired to remove the denture from the mandible. A single surface of interference is provided between the male and female members, so as to retain the denture onto the mandible. Moreover, the interference between male and female member is effected by a pair of arcuate surfaces, and maintained by a spring.

Because of the pressures exerted during chewing (i.e., high magnitude, from any direction), it is believed that denture attachment systems having single surfaces of interference may be subjected to the undesired detachment of the denture from the mandible. Moreover, in the system of U.S. Pat. No. 5,716,214, the pressures exerted on the denture are potentially transmitted against the biasing action of the spring because of the contact between the arcuate surfaces of the male and female members. This may ultimately lead to the disconnection of the denture from the implant.

SUMMARY OF THE INVENTION

It is therefore an aim of the present invention to provide a novel denture attachment system.

It is a further aim of the present invention to provide a denture attachment system which overcomes the disadvantages of the prior art.

Therefore, in accordance with the present invention, there is provided a denture attachment system comprising: an implant member adapted to be secured in a mandible such that a head of the implant member projects out of the mandible; and a locking mechanism adapted to be received in a denture so as to cooperate with the implant member to releasably secure the denture to the implant member, the locking mechanism having: a receptacle for receiving the head of the implant member; and a locking member being movable between a locking position in which the locking member blocks an access out of the receptacle by opposing a surface complementary to the shape of the head of the implant member to hold the implant member captive in the receptacle with points of contact between the head of the implant member and the locking member being diametrically opposed with respect to the head, and a release position in which the head of the implant member may enter/exit the receptacle.

Further in accordance with the present invention, there is provided a denture attachment system comprising: an implant member adapted to be secured in a mandible such that a head of the implant member projects out of the mandible; and a locking mechanism adapted to be received in a denture so as to cooperate with the implant member to releasably secure the denture to the implant member, the locking mechanism having: a receptacle for receiving the head of the implant member along an axis of insertion; and a locking member being movable in a plane of actuation between a locking position in which the locking member blocks an access to and out of the receptacle by opposing a surface complementary to the shape of the head of the implant member to hold the implant member captive in the receptacle, and a release position in which the head of the implant member may enter/exit the receptacle, the locking mechanism being configured such that the axis of insertion is generally normal to the plane of actuation.

BRIEF DESCRIPTION OF THE DRAWINGS

FIG. 3 is an exploded view of the locking mechanism of the denture attachment system of FIG. 2;

FIG. 4 is a perspective view of a seat member of the locking mechanism of FIG. 2;

FIG. 5 is a perspective view of a guillotine member of the locking mechanism of FIG. 2;

DESCRIPTION OF THE PREFERRED EMBODIMENTS

Figure 2:
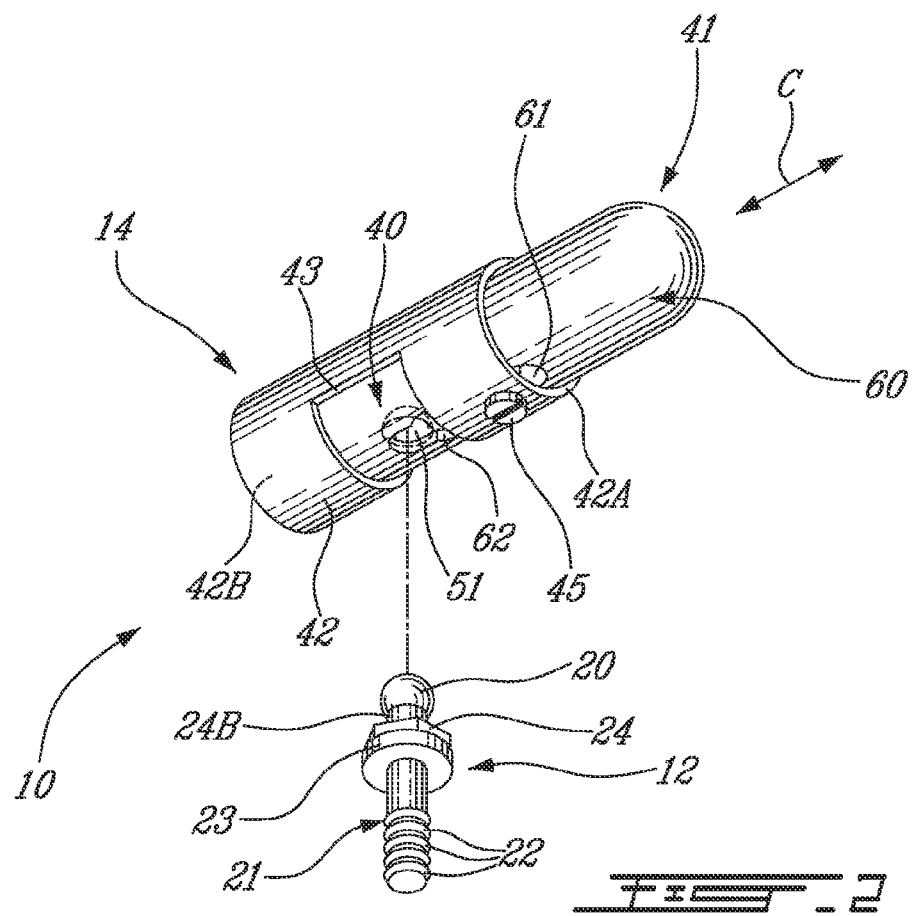
FIG. 2 is an exploded view of a locking mechanism with respect to an endosseous implant abutment, both of the denture attachment system, in position for a subsequent connection therebetween.

Referring to the drawings and, more particularly, to FIG. 2, a denture attachment system in accordance with a preferred embodiment is generally shown at 10. The system 10 has an endosseous implant, partly illustrated at 12, and a locking mechanism 14. It is pointed out that the endosseous implant illustrated herein includes an implant portion (not shown)

received in the osseous material, and an endosseous implant abutment illustrated at 12, supported by the implant portion. One-piece implants could be used with the denture attachment system. As will be described hereinafter, the endosseous implant abutment 12 and the locking mechanism 14 cooperate so as to releasably secure a denture (i.e., a dental prosthesis) to a mandible (or maxillary) of a user person.

Figure 1:
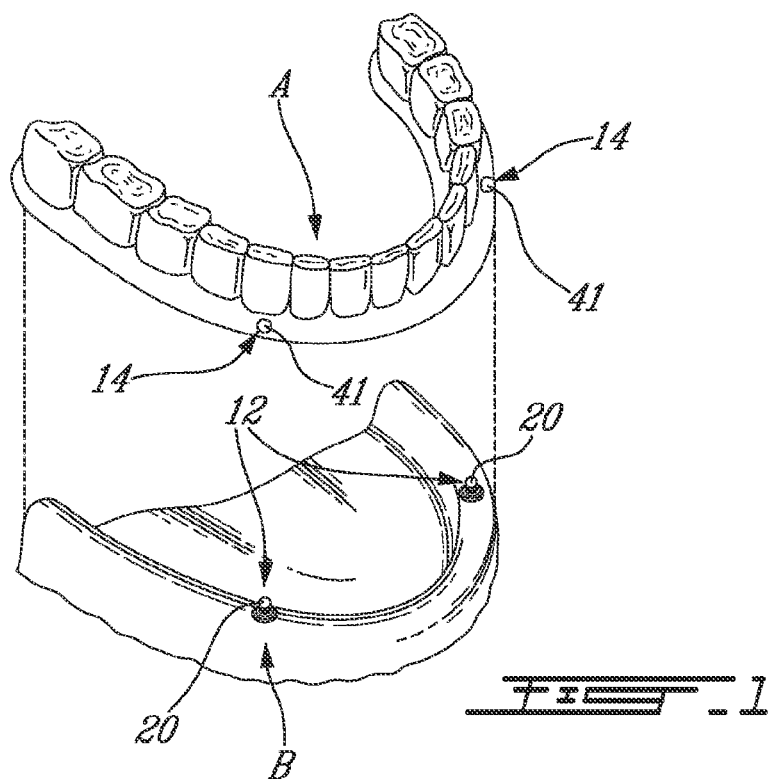
FIG. 1 is an exploded view of a denture with respect to a mandible, for subsequent connection therebetween using a denture attachment system in accordance with a preferred embodiment of the present invention.

Referring to FIG. 1, a denture A is shown placed above a mandible B. The denture A is secured to the mandible B by a pair of the denture attachment system 10 (FIG. 2). Accordingly, two endosseous implants (the implant abutments being visible at 12) are anchored in the osseous material of the mandible B, and will be used as anchors for the denture A onto the mandible B. Two locking mechanisms 14 protrude out of the denture A, and will releasably lock the denture A onto the mandible B.

Referring to FIG. 2, the endosseous implant abutment 12 is shown having a ball head 20 at an end of a stem 21. According to a preferred embodiment, the ball head 20 has a spherical geometry.

According to a preferred embodiment, the stem 21 has a cylindrical body, with threading 22 on the outer surface or any other suitable surface for anchoring the stem 21 in the mandible or maxillary. An abutment flange 23 is adjacent to the ball head 20. In an embodiment, a hexagonal head 24 (with neck 24B) is optionally positioned between the abutment flange 23 and the ball head 20.

When the implant abutment 12 is received in the mandible B as illustrated in FIG. 1, the stem 21 is screwed in the implant portion (not shown) implanted in the osseous material up to the abutment flange 23, which protrudes from the soft tissue of the mandible B. Accordingly, when the implant abutment 12 is anchored in the mandible B, the ball head 20 is exposed, as illustrated in FIG. 1.

The hexagonal head 24 provides grip (e.g., for tools such as a wrench) to affix or remove the implant abutment 12 from implant portion (not shown) in the mandible B.

Referring to FIG. 2, the locking mechanism 14 is typically housed in the acrylic base of the denture A (FIG. 1), such that a connection opening 40 thereof is exposed in a mandible receiving cavity of the denture A (i.e., at the underface of the denture A). Moreover, a detent end 41 faces outwardly from the base of the denture A, as shown in FIG. 1. The detent end 41, constituted by a detent end portion 64 of the guillotine. 60 FIG. 5, comes in different lengths. For instance, it is considered to provide the detent end 41 in three different sizes, to accommodate a lingual, normal or buccal position of the denture teeth depending on the three classical jaw relations (i.e., prognathic, normal, retrognathic).

Referring to FIG. 3, the locking mechanism 14 is shown in an exploded view. The locking mechanism 14 has a hollow cylindrical casing 42. The cylindrical casing 42 has an open end 42A, through which a cavity of the casing 42 is accessed, and a closed end 42B. An opening 43 is defined in the peripheral surface of the cylindrical casing 42, which opening will be part of the connection opening 40 of the locking mechanism 14. A tapped hole 44 is provided, so as to receive set screw 45 therein, or any suitable fastener.

Referring to FIG. 3, a biasing member 46 is received at the closed end 42B of the cavity of the casing 42. The biasing member 46 is typically a cushion of resilient material, or a spring.

Referring concurrently to FIGS. 3, 4 and 5, a seat member 50 and a guillotine member 60 are received one on another within the cylindrical cavity of the casing 42. Accordingly, the superposition of the seat member 50 and the guillotine member 60 defines a cylindrical body, sized so as to snugly fit within the cylindrical cavity of the casing 42.

The seat member 50 is a semi-cylinder having a hemispherical receptacle 51 on a flat surface thereof. A throughbore 52 is adjacent to the hemispherical receptacle 51. When assembled as illustrated in FIG. 2, the set screw 45 passes through the throughbore 52 of the seat member 50. The throughbore 52 is sized such that the seat member 50 is immovable when retained in the casing 42 by the set screw 45. In this position, the seat member 50 has the hemispherical receptacle 51 aligned with and facing toward the opening 43 in the casing 42.

Referring to FIGS. 3 and 5, the guillotine member 60 has a semi-cylinder portion 60A between a circular end 63 and a detent end portion 64, such that the seat member 50 and the guillotine member 60 form a cylindrical portion when the semi-cylinder position 60A and the seat member 50 are against one another. The semi-cylinder portion 60A has a greater length than the seat member 50, such that a translational degree of freedom is provided between the seat member 50 and the guillotine member 60 when the seat member 50 is abutted against the semi-cylinder position 60A, as shown in FIG. 3 by direction C.

The guillotine member 60 has an obround-shaped slot 61 (i.e., hockey-rink shape), as well as a generally pear-shaped slot 62 (e.g., with a circular portion and a throat portion). The guillotine member 60 is the movable member of the locking mechanism 14. More specifically, when the guillotine member 60 is received in the casing 42, the set screw 45 passes through the obround-shaped slot 61. The elongated shape of the obround-shaped slot 61 enables the translation of the guillotine member 60 along the directions illustrated by C in FIG. 2, between a locking position, and a release position.

The guillotine member 60 is sized such that the detent end portion 64 thereof extends out of the open end 42A of the casing 42, which end 64 is visible in FIG. 2. Moreover, the guillotine member 60 is configured such that the biasing member 46 biases the guillotine member 60 away from the closed end 42B through contact with the circular end 63, such that the guillotine member 60 has its end 64 extending out of the open end 42A of the casing 42. The detent end portion 64 of the guillotine member 60 will serve as detent to release the locking mechanism 14 from the implant abutment 12.

Figure 6A:
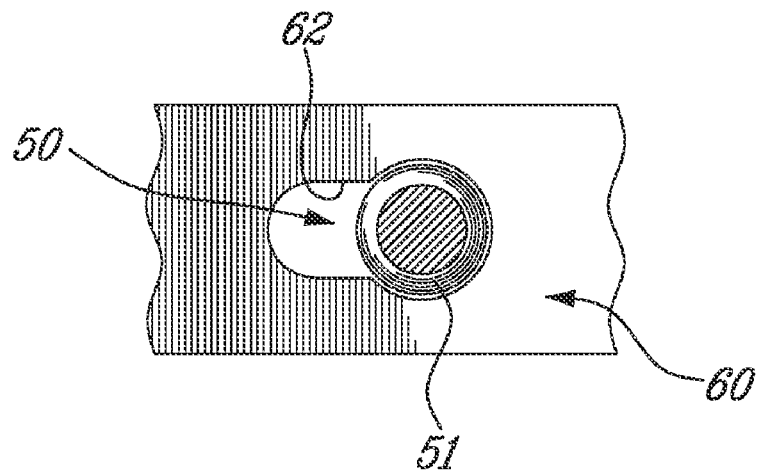
FIG. 6A is an enlarged view illustrating an interrelation between the guillotine member and the seat-member with the guillotine member in a release position.
Figure 6B:
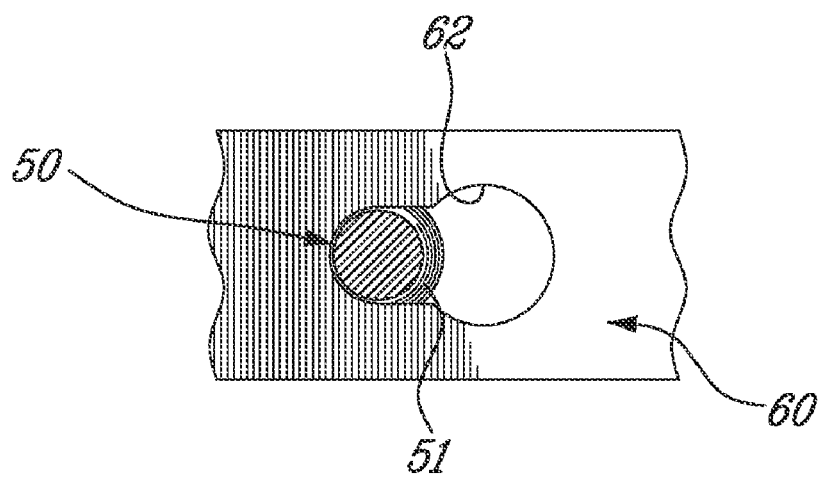
FIG. 6B is an enlarged view illustrating an interrelation between the guillotine member and the seat member with the guillotine member in a locking position.

Referring to FIGS. 6A and 6B, enlarged views illustrate the relative positions between the pear-shaped slot 62 of the guillotine member 60, and the hemispherical receptacle 51 of the seat member 50, when the seat member 50 and the guillotine member 60 are superposed in the casing 42, as illustrated in FIG. 2. These relative positions are the opposed limits associated with the translation of the guillotine member 60 with respect to the seat member 50.

In FIG. 6A, the guillotine member 60 is in its release position with respect to the seat member 50, whereby the larger end of the pear-shaped slot 62 is in register with the hemispherical receptacle 51. In the release position, the ball head 20 of the implant abutment 12 may access the hemispherical receptacle 51, so as to be lodged therein. In order for the guillotine member 60 to reach the release position of FIG. 6A, pressure must be exerted on the detent end portion 64 of the guillotine member 60, against the biasing action of the biasing member 46. When the pressure on the detent end portion 64 of the guillotine member 60 is released, the guillotine member 60 returns to its locking position, illustrated in FIG. 6B.

In FIG. 6B, the guillotine member 60 is in its locking position with respect to the seat member 50, whereby the narrower end of the pear-shaped slot 62 is in register with the hemispherical receptacle 51. In the locking position, the ball head 20 (not shown in FIG. 6B) is held captive in the hemispherical receptacle 51 by the periphery of the narrower end of the pear-shaped slot 62. More precisely, the width of the narrower end of the pear-shaped slot 62 is less than the diameter of the ball head 20 (FIG. 2), such that the ball head 20 lodged in the hemispherical receptacle 51 is held captive therein with the neck 24B passing through the narrower end of the pair-shaped slot 62. The surface of the guillotine member 60 (within the pear-shaped slot 62) that contacts the ball head 20 may be carved so as to match the surface of the ball head 20, to ensure the integrity of the fit between the ball head 20 as retained by the guillotine member 60. Alternatively, the pear-shaped slot 62 could oppose a pair of flat surfaces to the ball head 20, thereby providing two points of interference between the ball head 20 and the periphery of the pear-shaped slot 62, so as to enhance the integrity of the connection between the implant abutment 12 and the locking mechanism 14.

As the biasing member 46 biases the guillotine member 60 to the locking position of FIG. 6B, the ball head 20 will be held captive within the hemispherical receptacle 51, until the detent end portion 64 of the guillotine member 60 is pressed.

The ball head 20 will access the hemispherical receptacle 51 through the connection opening 40 illustrated in FIG. 2, and oriented in the denture toward the mandible supporting the implant abutment 12.

Therefore, in order to install the denture A onto the mandible B, the denture A is positioned above the mandible B as illustrated in FIG. 1, with the implant abutments 12 in the mandible B and the locking mechanisms 14 in the denture A having been relatively positioned with respect to one another in view of their cooperation.

Thereafter, the denture A is brought down onto the mandible B, such that the ball heads 20 of the implant abutments 12 are received in the connection openings 40 in the locking mechanisms 14 (FIG. 2).

The detent end portion 64 of the guillotine member 60 is pressed inwardly, so as to bring the guillotine member 60 to its release position (FIG. 6A), such that the ball head 20 of the implant abutment 12 may be lodged in the hemispherical receptacle 51 of the seat member 50. It is contemplated to provide the locking mechanism 14 with a quick connect configuration. For instance, the periphery of the pear-shaped slot 62 may be bevelled in order to momentarily force the guillotine member 60 toward the release position as a function of pressure exerted thereon by the ball head 20. In such an embodiment, the user person would not need to press the detent end 41 of the guillotine member 60 to install the denture A.

Once the ball head 20 of the implant abutment 12 is lodged in the hemispherical receptacle 51 of the seat member 50, the guillotine member 60 returns to its locking position through the action of the biasing member 46, whereby the implant abutment 12 is connected to the locking mechanism 14, and the denture A is releasably secured to the mandible B (FIG. 1).

In order to remove the denture A from the mandible B (FIG. 1), the detent end portion 64 of the guillotine member 60 is pressed such that the guillotine member 60 reaches its release position (FIG. 6A). The denture A may thus be lifted away from the mandible B, with the ball head 20 of the implant abutment 12 exiting through the connection opening 40 of the locking mechanism 14.

Advantageously, the two diametrically opposed points of interference (i.e., contact) between the ball head 20 and the guillotine member 60 reduce the risk of the unwanted disconnection of the locking mechanism 14 from the endosseous implant abutment 12.

It is contemplated to provide the denture attachment system 10 in various configurations. For instance, the use of a ball head 20 is described for implant abutment 12, but other geometries (e.g., conical, frusto-conical, cubic, and the like) could be used. Circular sections are preferred in that they often do not require to be in a given orientation for cooperation with a locking mechanism.

The biasing member 46 (FIG. 3) may be of various types. For instance, a resilient cushion member is preferably used, but it is contemplated to use a spring or the like. In the preferred embodiment, in order to enhance the biasing action of the resilient cushion, the latter may have given geometries, such as a hollow hourglass-shaped cylinder. All components of the denture attachment system 10 of the present invention are made of materials well suitable to the oral environment.

It is pointed out that the degree of freedom of the guillotine member 60 is generally transverse to the lockable degree of freedom between the locking mechanism 14 and the implant abutment 12. More specifically, the axis of insertion of the implant abutment 12 in the locking mechanism 14 is generally normal to a plane in which the guillotine member 60 is displaceable (i.e., actuation plane).

Although two denture attachment systems 10 of the present invention are illustrated in FIG. 1, it is pointed out that a denture could be connected to a mandible with one of more of the denture attachment system 10 of the present invention. The denture attachment system 10 of the present invention may be used for both the mandible and the maxillary.

The invention claimed is:

1. A denture attachment system comprising:
   an implant member having a stem adapted to be secured in a mandible such that a head at the end of the stem of the implant member projects out of the mandible, the head of the implant member being generally spherical in shape; and
   a locking mechanism adapted to be received in a denture so as to cooperate with the implant member to releasably secure the denture to the implant member, the locking mechanism having:
      a receptacle for receiving the head of the implant member; and
      a locking member being movable between a release position in which the head of the implant member may enter/exit the receptacle, and a locking position in which the locking member blocks an access out of the receptacle by opposing a hemispherical surface complementary to the shape of the head of the implant member, the locking member holding the implant member captive in the receptacle with points of contact between the head of the implant member and the locking member, a pair of the points of contact being located on diametrically opposed sides of the junction between the stem and the head of the implant member.

2. The denture attachment system according to claim 1, comprising a biasing member biasing the locking member to the locking position.

3. The denture attachment system according to claim 1, wherein the locking member has a guillotine member having a pear-shaped opening, a circular portion being in register with the receptacle in the release position of the locking member, and a throat portion being in register with the receptacle in the locking position of the locking member such that the throat portion defines the points of contact diametrically opposed with respect to the head.

4. The denture attachment system according to claim 1, wherein the locking mechanism has a cylindrical casing accommodating the receptacle and the locking member in the denture.

5. The denture attachment system according to claim 4, wherein the locking member has a semi-spherical detent end protruding out of the cylindrical casing for manual actuation of the locking member to the release position.

6. The denture attachment system according to claim 4, wherein the locking member is a guillotine member having a cylindrical body received in the cylindrical casing, and having a semi-cylindrical body portion defined in the cylindrical body, whereby the receptacle is lodged between the semi-cylindrical body portion and the cylindrical casing.

7. The denture attachment system according to claim 6, wherein the receptacle is defined in a semi-cylinder complementarily shaped to be received opposite the semi-cylindrical body portion of the locking member, the semi-cylinder being sized longitudinally so as to allow displacement of the locking member between the locking position and the release position.

8. The denture attachment system according to claim 1, wherein the head of the implant member is received in the receptacle along an axis of insertion, and the locking member is displaceable in a plane of actuation, the axis of insertion being generally normal to the plane of actuation.

9. A denture attachment system comprising:
an implant member adapted to be secured in a mandible such that a head of the implant member projects out of the mandible; and
a locking mechanism adapted to be received in a denture so as to cooperate with the implant member to releasably secure the denture to the implant member, the locking mechanism having:
a cylindrical casing;
a receptacle accommodated in the cylindrical casing for receiving the head of the implant member along an axis of insertion; and
a locking member accommodated in the cylindrical casing and being movable in a plane of actuation between a locking position in which the locking member blocks an access to and out of the receptacle by opposing a surface complementary to the shape of the head of the implant member to hold the implant member captive in the receptacle, and a release position in which the head of the implant member may enter/exit the receptacle, the locking mechanism being configured such that the axis of insertion is generally normal to the plane of actuation, wherein the locking member is a guillotine member having a cylindrical body received in the cylindrical casing, and having a semi-cylindrical body portion defined in the cylindrical body, whereby the receptacle is lodged between the semi-cylindrical body portion and the cylindrical casing.

10. The denture attachment system according to claim 9, comprising a biasing member biasing the locking member to the locking position.

11. The denture attachment system according to claim 9, wherein the locking member has a semi-spherical detent end protruding out of the cylindrical casing for manual actuation of the locking member to the release position.

12. The denture attachment system according to claim 9, wherein the receptacle is defined in a semi-cylinder complementarily shaped to be received opposite the semi-cylindrical body portion of the locking member, the semi-cylinder being sized longitudinally so as to allow displacement of the locking member between the locking position and the release position.

13. The denture attachment system according to claim 9, wherein the head of the implant member is generally spherical.

14. A denture attachment system comprising:
an implant member with a stem adapted to be secured in a mandible such that a head at the end of the stem of the implant member projects out of the mandible; and
a locking mechanism adapted to be received in a denture so as to cooperate with the implant member to releasably secure the denture to the implant member, the locking mechanism having:
a receptacle for receiving the head of the implant member; and
a locking member being movable between a locking position in which the locking member blocks an access out of the receptacle by opposing a surface complementary to the shape of the head of the implant member to hold the implant member captive in the receptacle with points of contact between (1) a junction of the stem and of the head of the implant member and (2) the locking member being diametrically opposed with respect to the implant member, and a release position in which the head of the implant member may enter/exit the receptacle, the locking member having a guillotine member with a pear-shaped opening, a circular portion being in register with the receptacle in the release position of the locking member, and a throat portion being in register with the receptacle in the locking position of the locking member such that the throat portion defines the points of contact diametrically opposed with respect to the head.

* * * * *